US010765671B2

(12) United States Patent
Kottayil et al.

(10) Patent No.: US 10,765,671 B2
(45) Date of Patent: *Sep. 8, 2020

(54) STABLE NIMODIPINE PARENTERAL FORMULATION

(71) Applicant: NORTIC HOLDINGS INC., East Brunswick, NJ (US)

(72) Inventors: S. George Kottayil, West Windsor, NJ (US); Amresh Kumar, Plainsboro, NJ (US); Prasanna Sunthankar, West Windsor, NJ (US); Vimal Kavuru, Holmdel, NJ (US)

(73) Assignee: NORTIC HOLDINGS INC., East Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/046,476

(22) Filed: Jul. 26, 2018

(65) Prior Publication Data

US 2018/0325886 A1 Nov. 15, 2018

Related U.S. Application Data

(63) Continuation of application No. 15/485,813, filed on Apr. 12, 2017, now Pat. No. 10,092,557.

(60) Provisional application No. 62/322,008, filed on Apr. 13, 2016.

(51) Int. Cl.
| A61K 31/455 | (2006.01) |
| A61K 31/4422 | (2006.01) |
| A61K 47/10 | (2017.01) |
| A61K 47/24 | (2006.01) |
| A61K 47/26 | (2006.01) |
| A61K 47/44 | (2017.01) |
| A61K 9/00 | (2006.01) |
| A61K 9/107 | (2006.01) |

(52) U.S. Cl.
CPC .......... *A61K 31/455* (2013.01); *A61K 9/0019* (2013.01); *A61K 9/1075* (2013.01); *A61K 31/4422* (2013.01); *A61K 47/10* (2013.01); *A61K 47/24* (2013.01); *A61K 47/26* (2013.01); *A61K 47/44* (2013.01)

(58) Field of Classification Search
CPC .. A61K 31/455; A61K 9/0019; A61K 9/1075; A61K 47/10; A61K 47/26
See application file for complete search history.

(56) References Cited

U.S. PATENT DOCUMENTS

| 4,879,308 A | 11/1989 | Alam et al. |
| 5,114,956 A | 5/1992 | Hoff |
| 5,858,410 A * | 1/1999 | Muller .................. A61K 9/0019 424/489 |
| 2004/0180005 A1* | 9/2004 | Jurgens ................ A61K 9/1075 424/46 |
| 2004/0247624 A1 | 12/2004 | Unger et al. |
| 2007/0117851 A1 | 5/2007 | Remenar et al. |
| 2009/0253722 A1 | 10/2009 | Gillessen et al. |
| 2012/0177699 A1* | 7/2012 | Tong ..................... A61K 9/107 424/400 |
| 2013/0156853 A1 | 6/2013 | Zhang et al. |
| 2014/0296191 A1 | 10/2014 | Patel et al. |

FOREIGN PATENT DOCUMENTS

| CN | 1480140 A | 3/2004 |
| CN | 1589795 A * | 3/2005 |
| CN | 101129366 | 2/2008 |
| CN | 101129366 A * | 2/2008 |
| CN | 101129366 A | 2/2008 |
| CN | 102525917 | 7/2012 |
| JP | S59206305 | 11/1984 |

OTHER PUBLICATIONS

English Translation of CN-101129366-A from Google Patents. Translated on Oct. 16, 2017. (Year: 2017).*
English Translation of CN-1589795-A from Google Patents. Translated on Jun. 5, 2019. (Year: 2019).*
International Search Report from the International PCT Application No. PCT/US19/18945 dated Apr. 24, 2019.
Teagarden, DL, et al. "Freeze Drying/Lyophilization of Pharmaceutical and Biological Products" Informa healthcare. Drugs and The Pharmaceutical Sciences, Third Edition, 2010, vol. 206; 276, Miscellaneous Pharmaceutical Uses—Liposomes section.
Wikipedia, Polysorbate, Jan. 29, 2016, p. 1/2; <https://en.wikipedia.org/wiki/Polysorbate>.
Kalepu et al. "Insoluble drug delivery strategies: review of recent advances and business prospects" Acta Pharmaceutica Sinica B, vol. 5, No. 5, pp. 442-453; p. 445 (May 26, 2015).
Stagliano "Do mirrors reflect ultraviolet light?" (Dec. 24, 2014), <https://www.quora.com/Do-mirrors-reflect-ultraviolet-light>.
International Search Report from International PCT Application No. PCT/US2017/027164 dated Jul. 21, 2017.
Pizarro et al. "Photophysical and photochemical behavior of nimodipine and felodipine" Journal of Photochemistry and Photobiology A: Chemistry, Jun. 10, 2007, vol. 189, pp. 23-29; p. 23.
International Search Report from International PCT Application No. PCT/US2018/40038 dated Aug. 31, 2018.
"Nimotop 0.02% Solution for Infusion" Summary of Product Characteristics (SmPC)—(eMC) https://www.medicines.org.uk/emc/product/1366/smpc pp. 1-9; date of first authorization: Jan. 21, 1988/ Nov. 23, 2003/ Date of revision of the text Aug. 31, 2017.

(Continued)

*Primary Examiner* — Doan T Phan
(74) *Attorney, Agent, or Firm* — Davidson, Davidson & Kappel, LLC

(57) ABSTRACT

A nimodipine injection concentrate and diluted formulation comprises nimodipine (base or salt), an effective amount of a hydrophilic surfactant, and a pharmaceutically acceptable carrier for injection which is an aqueous solution, an organic solvent, an oil, or a cyclodextrin, such that the nimodipine is substantially contained in a concentrated injection solution, suspension, emulsion or complex as a micelle or a colloidal particle or an inclusion complex and the formulation is stable and clear. In certain embodiments, the hydrophilic surfactant is polysorbate 80.

29 Claims, 4 Drawing Sheets

(56) References Cited

OTHER PUBLICATIONS

"Nimotop (nimodipine) Capsules for Oral Use" FDA approved Labeling text, Bayer Pharmaceuticals Corporation, pp. 1-8 (Dec. 2005).
"Product Information Nimotop nimodipine" Bayer Australia Ltd; (Jun. 9, 1993); date of most recent amendment (Apr. 18, 2017).
European Search Report from corresponding European Application No. EP 17 78 3039 dated Oct. 16, 2019.
International Written Opinion from corresponding International PCT Application No. PCT/US2018/040038 dated Aug. 18, 2018.

* cited by examiner

STABLE NIMODIPINE PARENTERAL FORMULATION

FIELD OF THE INVENTION

The present invention provides a stable preservative free nimodipine parenteral solution suitable for continuous intravenous (IV) administration. The parenteral solution composition consists of nimodipine (concentrations ranging from about 0.01 to about 5 mg/ml), a hydrophilic surfactant and a co-solvent, preferably ethanol. The final concentration of ethanol in the administered formulation is preferably less than about 2% w/v.

BACKGROUND OF THE INVENTION

Nimodipine, a lipid soluble substituted 1,4-dihydropyridine with vasodilatatory properties, is indicated for prophylaxis and treatment of ischemic neurologic deficits caused by cerebral vasospasms after subarachnoid hemorrhage (SAH). Currently, nimodipine treatment of ischemic brain injury is the first-line treatment. In man, nimodipine is rapidly absorbed after oral administration, and peak concentrations are generally attained within one hour. The terminal elimination half-life is approximately 8 to 9 hours but earlier elimination rates are much more rapid, equivalent to a half-life of 1-2 hours; a consequence is the need for frequent (every 4 hours) dosing. Nimodipine is eliminated almost exclusively in the form of metabolites and less than 1% is recovered in the urine as unchanged drug. Numerous metabolites, all of which are either inactive or considerably less active than the parent compound, have been identified. Because of a high first-pass metabolism, the bioavailability of nimodipine averages 13% after oral administration. The bioavailability is significantly increased in patients with hepatic cirrhosis, with Cmax approximately double that in normal, which necessitates lowering the dose in this group of patients.

Currently approved products in the US market are oral solid and liquid dosage forms of nimodipine. Nimodipine is marketed in the US as an oral dosage form, NIMOTOP® liquid-filled capsules (Bayer Pharmaceuticals Corp.) and equivalent generics. NIMOTOP® capsules and generic versions of the same each contain 30 mg of nimodipine and are commonly administered in a two-capsule 60 mg dose, and dosed every 4 hours. In the event that a patient is unconscious or unable to swallow, the nimodipine capsule contents are extracted by syringe and administered via an intraoral or an intranasal (e.g., naso-gastric) tube. The medical practitioner administering the dose may either unknowingly or due to improper handling, extract less than the full amount of the liquid dose from the capsule, thus introducing substantial risk of incomplete dosing and placing undue burden on medical professionals. The incomplete dosing is exacerbated by the relatively small dosage volumes involved and high drug concentration of drug in the commercially available capsules. Hence, a practitioner's failure to dose the full amount of the high-concentration, small volume liquid from the commercial capsules could lead to a significant under dose of nimodipine. Also, the FDA has noted in warnings related to oral nimodipine administration via nasogastric tubes that because a standard needle does not fit on an oral syringe, the formulation within a capsule is extracted using an intravenous syringe. The use of intravenous syringes to extract nimodipine formulation from the capsule increases the chance of medication being inadvertently administered intravenously instead of by mouth or nasogastric tube.

To quickly and effectively treat or control disease progression following SAH, intravenous administration of nimodipine is usually preferred. Intravenous (IV) Nimodipine is approved in Europe and marketed in Europe by Bayer under the trade name Nimotop®. The current commercially marketed injectable nimodipine (Bayer's Nimotop®) available in Europe and other regulated markets contains large amounts of organic solvent—about 23.7% ethanol and 17% polyethylene glycol 400. The large amount of ethanol in Nimotop is harmful for those suffering from alcoholism or impaired alcohol metabolism and in pregnant or breast feeding women. Also, high concentrations of ethanol may cause pain and irritation at the injection site. IV Nimotop is most often infused continuously up to three weeks. Due to the high alcohol content in Bayer's IV Nimotop solution, it is diluted by co-infusing saline and dextrose by way of a three-way stopcock.

Nimodipine has poor water solubility and is therefore difficult to formulate as an aqueous injectable. That is the reason that Nimotop IV infusion solution utilizes up to 23.7% of alcohol as a co-solvent to solubilize nimodipine.

U.S. Pat. No. 5,114,956 describes parenteral formulations containing nimodipine, that contain 0.01-0.4% by weight of nimodipine, relative to 100 parts by weight of a solvent consisting of 30-70% by weight, preferably 45-70% by weight, of water, 15-40% by weight, preferably 15-30% by weight, of propylene glycol and/or polyethylene glycol, preferably with a mean molecular weight of 200, 400 and 600, 15-30% by weight, preferably 15-25% by weight, of ethanol, and, where appropriate, customary auxiliaries and/or additives.

Through its Adverse Event Reporting System (AERS) and other sources, including published literature, the FDA has identified 31 cases of nimodipine errors between 1989 and 2009, with 25 involving the administration of the contents of the oral capsule intravenously according to the FDA. Four patients who received nimodipine intravenously died, while another 5 suffered severe reactions and one patient suffered permanent harm, according to the agency.

There exists an unmet medical need for an easy to administer nimodipine dosage form for patients who find it difficult or are unable to swallow and patients who are unconscious. An additional imperative is the need to eliminate serious life threatening medication errors as a result of improper administration of drug.

OBJECTS AND SUMMARY OF THE INVENTION

The present invention aims to resolve solubility deficiencies of previously approved nimodipine dosage forms by the development of a robust, stable, and easy to administer nimodipine infusion injection. Another objective of the present invention is to provide the composition and preparation of the nimodipine infusion solution and its administration.

In accordance with the above objects and others, the invention is further directed in part to a nimodipine concentrate formulation, comprising nimodipine base or a pharmaceutically acceptable salt of nimodipine in a concentration from about 0.01 or from about 0.5 mg/ml to about 5 mg/ml; an organic solvent; an aqueous carrier; and an effective amount of a hydrophilic surfactant, such that nimodipine in the concentrate formulation is contained in micelles. In certain preferred embodiments, the invention is directed in part to a nimodipine injection concentrate formulation, comprising nimodipine in a concentration from about 0.5 mg/ml to about 5 mg/ml; an organic solvent in an amount greater than 30% to about 90%, w/w; from about 0.005 to about 30%, preferably from about 0.5% or 1% to about 15% of a hydrophilic surfactant, and a pharmaceutically acceptable aqueous carrier for injection comprising from about 30 to about 80% of the concentrate formulation, such that nimodipine in the concentrate is contained in micelles. In preferred embodiments, the formulation is stable and clear. In certain embodiments, the hydrophilic surfactant is polysorbate 80. In certain embodiments, the pharmaceutically acceptable carrier is water for injection, and the nimodipine is substantially contained within micelles. In certain preferred embodiments, the organic solvent comprises or consists of ethanol. In certain embodiments, a unit dose of the concentrate is diluted to a total volume of 5 ml with water for injection and enclosed within a pharmaceutically acceptable container, e.g., an ampule or vial. In certain embodiments, the nimodipine injection concentrate, further comprises an effective amount of a preservative. In certain preferred embodiments of the nimodipine injection concentrate, the median particle size of micelles or nano-emulsions ranges from about 0.5 nanometer to about 350 nanometers, or from about 0.5 nm to about 200 nm, or from about 5 nm to about 50 nm. Preferably, the nimodipine concentrate formulation is clear and does not contain a crystal nimodipine precipitate. In certain preferred embodiments, the nimodipine is substantially contained within micelles as a nano-emulsion. The invention is further directed in part to the nimodipine concentrate formulation of the present invention (e.g., as described above), which is diluted in a suitable injection medium, such that the diluted formulation for injection contains less than about 2% or preferably less than about 1% w/v organic solvent (e.g., alcohol). In preferred embodiments, the solution is predominantly an aqueous medium, the diluted injection medium remaining a clear solution that displays no precipitate of nimodipine. In preferred embodiments, the concentrate when diluted in a suitable injection medium allows for parenteral administration of a single 250 ml infusion bag or bottle to a human patient, the diluted formulation containing less than about 2% or preferably less than about 1% w/v organic solvent (e.g., alcohol). In certain embodiments, the concentrate and diluted solution further comprise an effective amount of a pharmaceutically acceptable preservative. In certain preferred embodiments, substantially all or all of the nimodipine contained in the formulation is contained in micelles.

In other embodiments, the invention is directed in part to a nimodipine injection concentrate formulation, comprising nimodipine in a concentration from about 0.5 mg/ml to about 5 mg/ml, from about 1% to about 15% of a hydrophilic surfactant, and a pharmaceutically acceptable carrier for injection comprising from about 10% to about 90% of the formulation injection concentrate, the pharmaceutically acceptable carrier for injection selected from the group consisting of an aqueous solution, an organic solvent, an oil, and a cyclodextrin, such that the nimodipine is substantially contained in a concentrated injection solution, suspension, emulsion or complex as a micelle or a colloidal particle or an inclusion complex and the formulation is stable and clear. In certain embodiments, the hydrophilic surfactant is polysorbate 80. In certain embodiments, the pharmaceutically acceptable carrier is water for injection, further comprising from about 0.5% to about 30% of a pharmaceutically acceptable hydrophilic surfactant (alternatively referred to as an emulsifier herein), and the nimodipine is substantially contained within micelles. In other embodiments, the pharmaceutically acceptable carrier is an organic solvent, and the concentrate further comprises water for injection. In other embodiments, the pharmaceutically acceptable carrier is an oil, further comprising from about 0.005% to about 30%, more preferably from about 0.5 to about 15%, of a pharmaceutically acceptable hydrophilic surfactant, and the nimodipine is substantially contained within micelles. In certain preferred embodiments, the hydrophilic surfactant (emulsifier) is selected from the group consisting of a phospholipid and a polyethylene glycol. In certain embodiments, a unit dose of the concentrate is diluted to a total volume of 5 ml with water for injection and enclosed within a pharmaceutically acceptable container, e.g., an ampule or vial. In certain embodiments, the nimodipine injection concentrate, further comprises an effective amount of a preservative. In certain preferred embodiments of the nimodipine injection concentrate, the median particle size of micelles or nano-emulsions ranges from about 0.5 nanometer to about 350 nanometers, or from about 0.5 nm to about 200 nm, or from about 5 nm to about 50 nm. Preferably, the nimodipine concentrate formulation is clear and does not contain a crystal nimodipine precipitate. Preferably, the nimodipine concentrate formulation is stable. In certain preferred embodiments, the nimodipine is substantially contained within micelles as a nano-emulsion.

The invention is further directed in part to a directly infusible nimodipine formulation (without dilution; e.g., suitable for parenteral administration) in humans, comprising nimodipine in a concentration from about 0.01 mg/ml to about 1.0 mg/ml, a pharmaceutically acceptable carrier (e.g., for injection) selected from the group consisting of an aqueous solution, an organic solvent, an oil, and a cyclodextrin, the formulation comprising a volume from about 50 ml to about 1000 ml and contained in a pharmaceutically acceptable container (e.g., a bag or vial), wherein when present the organic solvent preferably comprises less than 2% w/v or less than 1% w/v of the formulation, an effective amount of a hydrophilic surfactant such that the nimodipine is substantially contained in a diluted injection solution in micelles and the formulation remains a clear solution and displays no precipitation of nimodipine. In preferred embodiments the hydrophilic surfactant is from 0.01% to about 2.5% w/v of the directly infusible (ready-to-use) formulation. In certain embodiments, the hydrophilic surfactant is a non-ionic hydrophilic surfactant, in certain embodiments most preferably comprising or consisting of polysorbate 80. In certain embodiments, the organic solvent comprises or consists of ethanol. In certain preferred embodiments, the pharmaceutically acceptable aqueous carrier comprises water for injection. In certain preferred embodiments, the hydrophilic surfactant is included in an amount from about 0.01% to about 2.5% of the directly infusible formulation. In certain preferred embodiments, the formulation is stable when exposed to conditions of 40° C.±2° C./75% RH±5% RH for at least 6 months; or which is stable when exposed to conditions of 25° C.±2° C./60% RH±5% RH for at least 12 months. In certain preferred embodiments, the nimodipine is substantially contained within micelles as a nano-emulsion.

In other embodiments, the pharmaceutically acceptable carrier is a beta-cyclodextrin, wherein the nimodipine is substantially contained within an inclusion complex. In certain embodiments, a unit dose of the concentrate is diluted to a total volume of 5 ml with water for injection and enclosed within a pharmaceutically acceptable container, e.g., an ampule or vial. In certain preferred embodiments, the organic solvent comprises ethanol.

In embodiments of the invention in which an organic solvent is included in the pharmaceutically acceptable carrier, the organic solvent may comprise, e.g, at least 25% of the concentrate, and in certain embodiments at least 40% of the concentrate.

In certain preferred embodiments, the nimodipine concentrate has a volume from about 1 ml to about 10 ml, preferably about 5 ml, and is contained in an ampoule or vial.

In certain embodiments, the nimodipine injection concentrate is diluted with water for injection, saline, dextrose or other commonly available infusion solutions up to a concentration of 0.01 mg/ml remains a clear solution and displays no crystal precipitation of nimodipine. The nimodipine injection concentrate can preferably be diluted with a suitable injection medium that allows for administration of, e.g., a single 100 or preferably 250 ml infusion bag or bottle that contains, e.g., less than 1% w/v alcohol in a predominantly aqueous medium, the diluted injection medium remaining a clear solution that displays no precipitation of nimodipine.

The invention is further directed in part to a nimodipine formulation suitable for injection into humans, comprising nimodipine in a concentration from about 0.01 mg/ml to about 1.0 mg/ml, a pharmaceutically acceptable carrier (e.g., for injection) selected from the group consisting of an aqueous solution, an organic solvent, an oil, and a cyclodextrin, the formulation comprising a volume from about 50 ml to about 1000 ml, wherein when present the organic solvent preferably comprises less than 2% w/v of the formulation, an effective amount of a hydrophilic surfactant such that the nimodipine is substantially contained in a diluted injection solution, suspension, emulsion or complex as a micelle or a colloidal particle or an inclusion complex and the formulation remains a clear solution and displays no precipitation of nimodipine. In certain embodiments, the hydrophilic surfactant is polysorbate 80. In certain embodiments, the pharmaceutically acceptable carrier is an organic solvent, further comprising water for injection. In certain embodiments, the pharmaceutically acceptable carrier is an oil, further comprising from about 0.005% to about 30%, more preferably from about 0.5 to about 15%, and in certain embodiments from about 0.005% to about 3.0%, of a pharmaceutically acceptable hydrophilic surfactant (alternatively referred to as an emulsifier), and the nimodipine is substantially contained within micelles. In certain preferred embodiments, the nimodipine is substantially contained within micelles as a nano-emulsion.

In certain preferred embodiments, the emulsifier is selected from the group consisting of a phospholipid and a polyethylene glycol. In other embodiments, the pharmaceutically acceptable carrier is a beta-cyclodextrin, wherein the nimodipine is substantially contained within an inclusion complex. In certain preferred embodiments, the nimodipine formulation is contained within a single infusion bag or bottle for continuous intravenous infusion. In certain preferred embodiments of the nimodipine formulation, the median particle size of nimodipine micelles or nano-emulsions or complex ranges from about 0.5 nanometer to about 350 nanometers, or from about 0.5 nm to about 200 nm, or from about 5 nm to about 50 nm. Preferably, the nimodipine formulation is clear and does not contain a crystal nimodipine precipitate. Preferably, the nimodipine formulation is stable. The administration of the nimodipine formulation via injection or infusion allows first pass metabolism of the nimodipine by the liver to be minimized, and the nimodipine formulations administered via injection have significantly improved bioavailability as compared to oral nimodipine formulations. By virtue of the nimodipine injectable formulations of the invention, consistent levels of nimodipine can be maintained in the plasma and CSF of the (e.g., human) patient.

In alternative embodiments to the above, the nimodipine formulation is diluted with a suitable pharmaceutical carrier for oral or nasal ingestion (e.g., a suitable aqueous solution).

In certain preferred embodiments of the above-described nimodipine concentrate and formulation, the aqueous carrier is selected from the group consisting of Sodium Chloride Injection, Ringers Injection, Isotonic Dextrose Injection, Sterile Water Injection, Dextrose, and Lactated Ringers Injection.

In certain preferred embodiments of the above-described nimodipine concentrate and formulation, the oil is selected from the group consisting of fixed oils of vegetable origin, cottonseed oil, corn oil, sesame oil and peanut oil.

In certain preferred embodiments, the nimodipine formulation further comprises one or more preservatives. Examples of suitable preservatives include, e.g., phenols or cresols, mercurials, benzyl alcohol, chlorobutanol, methyl and propyl p-hydroxybenzoic acid esters, thimerosal, benzalkonium chloride, benzethonium chloride, boric acid, p-hydroxybenzoates, phenols, chlorinated phenolic compounds, alcohols, quarternary compounds, mercurials, and mixtures of any of the foregoing.

In further embodiments, the hydrophilic surfactant comprises from about 0.01% to about 2.5% of the formulation, and in certain preferred embodiments the hydrophilic surfactant comprises at least 0.1% in the diluted nimodipine formulation.

In certain preferred embodiments, the organic solvent comprises at least 1% of the formulation (diluted formulation).

In certain preferred embodiments, the pharmaceutically acceptable carrier comprises from about 0.1% to about 15% of the formulation.

In certain preferred embodiments, the nimodipine formulation has a pH from about 3 to about 9, and in certain preferred embodiments, preferably from about 4.5 to about 7.5 or 8.

In further embodiments, the invention is directed to a method of preparing a nimodipine formulation (concentrate) for intravenous administration, comprising mixing nimodipine in a concentration from about 0.5 mg/ml to about 5 mg/ml with a pharmaceutically acceptable carrier, such that the pharmaceutically acceptable carrier for injection comprises from about 10% to about 90% of the concentrate; thereafter adding from about 1% to about 15% of a hydrophilic surfactant to prepare a concentrated injection solution, suspension, emulsion or complex; and optionally adding from about 0.5 ml to about 4.0 ml of a pharmaceutically acceptable medium for injection to prepare a nimodipine concentrate formulation. Preferably, the nimodipine concentrate formulation is clear and does not contain a crystal nimodipine precipitate. The method may further comprise diluting the nimodipine concentrate in a pharmaceutically acceptable carrier for injection selected from the group consisting of an aqueous solution, an organic solvent, an oil, and a cyclodextrin to a volume from about 50 ml to about 1000 ml, wherein when present the organic solvent comprises less than 2% w/v of the formulation, and the formulation remains a clear solution and displays no crystalline precipitation of nimodipine. In certain preferred embodiments of the nimodipine concentrate or diluted formulation, the median particle size of nimodipine micelles or nano-emulsions or complex ranges from about 0.5 nanometer to about 350 nanometers, or from about 0.5 nm to about 200 nm, or from about 5 nm to about 50 nm.

The invention is further directed to a method of treating human patients having a condition selected from an aneurysm, subarachnoid hemorrhage, vasospastic angina, Prinzmetal angina, stable angina, acute myocardial infarction, myocardial arrest, arrhythmia, systemic hypertension, pulmonary hypertension, congestive heart failure, coronary artery surgery and hypertrophic cardiomyopathy, comprising continuously infusing an intravenous nimodipine solution in accordance with the present invention over a period of about three weeks. The nimodipine infusion rate may be, e.g., from about 0.05 mg nimodipine per hour to about 5 mg nimodipine per hour. In certain embodiments, the intravenous nimodipine dose is from about 2 to 10 mg administered every five hours. In certain embodiments, the nimodipine formulation is administered via intravenous bolus, intravenous infusion, intra-arterial, intraoral, or intranasal using a naso-gastric tube. In certain embodiments, the method further comprises further diluting to a $2.5 \times 10^{-5}$ mole solution of nimodipine to rinse the exposed arteries after clipping the aneurysm and before an intravenous infusion of nimodipine administered to improve patient outcome. The diluted formulation may be contained within an infusion set and bag. In further embodiments, the infusion bag is covered with ultraviolet light (UV) protective bags to further protect the nimodipine from photo-degradation. In other preferred embodiments, the nimodipine formulation is administered as a continuous infusion. In methods of the invention, first pass metabolism by the liver is minimized and bioavailability is improved. Consistent levels of nimodipine are therefore maintained in the plasma and CSF of the (e.g., human) patient.

The present invention relates to a novel pharmaceutical composition containing nimodipine base or any acceptable pharmaceutical salt as active for continuous parenteral administration.

The present invention available in particular in the form of a solution for parenteral administration that is a sterile preservative free premix ready for infusion with no further dilution required prior to administration.

The present invention available in particular in the form of a solution for parenteral administration that is in the form of a concentrated injectable solution which can be diluted down in an appropriate medium (e.g. saline) to a solution for administration by infusion.

As used herein, the term "unit dose" refers to physically discrete units suitable as unitary dosages for mammalian subjects, each unit containing as the active ingredient a predetermined quantity of the nimodipine. Examples of suitable unit doses of nimodipine in accordance with the invention include clear solution or micelles or nano-emulsion in suitable containers, e.g., in a ampule or vial.

The term "comprising" is an inclusive term interpreted to mean containing, embracing, covering or including the elements listed following the term, but not excluding other unrecited elements.

A "therapeutically effective amount" means the amount that, when administered to an animal for treating a disease, is sufficient to effect treatment for that disease.

As used herein, the term "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

By "stable", it is meant that substantially no degradation of the concentrate intravenous infusion solution (the product) is observed after storage for 1 month at 40° C. In preferred embodiments, the term "stable" with respect to the concentrate intravenous infusion solution comprising the water-insoluble nimodipine and surfactant(s) means that there is less than about 5% degradation (and preferably less than 4%, or less than 3%, or less than 2%, or less than 1.5%, or less than 1% degradation) of the nimodipine and no observable precipitate after storage for 48 hours; or that the nimodipine micelle structure is thermally stable during a terminal sterilization process by autoclaving at 121° C. for 30 minutes, in that the mean diameter of the colloidal structures does not change by more than about 50 nanometer comparing the colloidal structures before and after the terminal sterilization process, or both.

The term "parenteral" as used herein, includes subcutaneous injections, intravenous, intramuscular, intrasternal injection or infusion techniques.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

DETAILED DESCRIPTION

Figure 1:
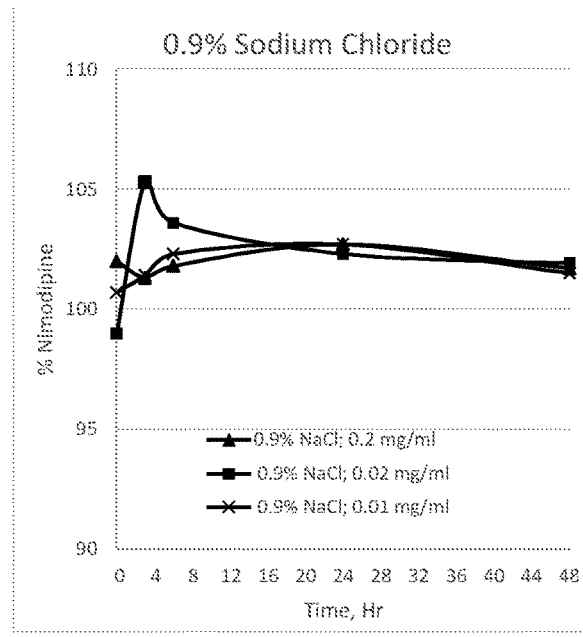
FIG. 1 is a graphical representation of the nimodipine concentration of the formulation of Example 3 at the tested concentrations (0.2 mg/ml, 0.02 mg/ml and 0.01 mg/ml) in 0.9% sodium chloride solution.

Nimodipine is a dihydropyridine calcium antagonist. Nimodipine is isopropyl 2-methoxyethyl 1,4-dihydro-2,6-dimethyl-4-(m-nitrophenyl)-3,5-pyridinedicarboxylate. It has a molecular weight of 418.5 and a molecular formula of $C_{21}H_{26}N_2O_7$. Nimodipine inhibits calcium ion transfer into these cells and thus inhibits contractions of vascular smooth muscle. The contractile processes of smooth muscle cells are dependent upon calcium ions, which enter these cells during depolarization as slow ionic transmembrane currents. In animal experiments, nimodipine had a greater effect on cerebral arteries than on arteries elsewhere in the body perhaps because it is highly lipophilic, allowing it to cross the blood-brain barrier; concentrations of nimodipine as high as 12.5 ng/mL have been detected in the cerebrospinal fluid of nimodipine-treated subarachnoid hemorrhage (SAH) patients. The precise mechanism of action of nimodipine in humans is unknown. Although the clinical studies demonstrate a favorable effect of nimodipine on the severity of neurological deficits caused by cerebral vasospasm following SAH, there is no arteriographic evidence that the drug either prevents or relieves the spasm of these arteries. However, whether or not the arteriographic methodology utilized was adequate to detect a clinically meaningful effect, if any, on vasospasm is unknown.

Nimodipine as a pale yellow crystalline powder almost insoluble in water (2.5 µg/ml, 25° C.) Therefore its intrinsic solubility poses challenges in the development of an injectable pharmaceutical formulation that is concentrated, stable and dilutable. The present invention aims to resolve solubility deficiencies of previously approved nimodipine dosage forms by the development of a robust, stable, and easy to administer nimodipine infusion injection. Another objective of the present invention is to provide the composition and preparation of the nimodipine infusion solution and its administration.

Two key aspects of a pharmaceutically acceptable liquid formulation, e.g., for parenteral use, are solubility of the drug in the carrier (solvent) and the stability of the final formulation (including but not limited to the ability of the formulation to prevent the drug from precipitating out of solution). The prior art is replete with examples of excipients used to solubilize poorly water soluble drugs for oral and injectable dosage forms. Such excipients include organic solvents, surfactants, triglycerides, cyclodextrins and phospholipids.

The use of organic solvents such as ethanol is limited for parenteral formulations because of possible precipitation of the active (drug), pain, inflammation and hemolysis upon injection. Ethanol is used for both solubility and stability reasons in the prior commercially available forms of nimodipine. As previously reported herein, the currently marketed nimodipine formulation in Europe includes 23.7% ethanol.

In contrast to prior intravenous nimodipine formulations, the intravenous nimodipine formulation of the present invention is a solution comprising nimodipine, a hydrophilic surfactant and a small quantity of organic solvent, wherein nimodipine is dissolved in a small amount of organic solvent by mixing and further this nimodipine solution is combined with a hydrophilic surfactant to form micelles of nimodipine in a clear solution.

The Concentrate

One aspect of the present invention is directed to a nimodipine injection concentrate. In such embodiments, the nimodipine is mixed with a pharmaceutically acceptable carrier to prepare a concentrated injection solution, suspension, emulsion or complex. Thereafter, an effective amount of a hydrophilic surfactant is added. Optionally, a pharmaceutically acceptable medium for injection is added in a relatively small quantity (e.g., 5 ml) in order to prepare the final nimodipine concentrate formulation.

In one embodiment of the invention, the concentrate may be prepared by dissolving the nimodipine in a small amount of organic solvent, e.g., by mixing. Thereafter, in certain preferred embodiments, the resulting nimodipine solution is combined with an effective amount of a hydrophilic surfactant to form micelles of nimodipine in a clear solution. Thereafter, a suitable pharmaceutical medium for injection (e.g., water for injection) is added to prepare the final nimodipine concentrate formulation. In certain preferred embodiments, the organic solvent may be, e.g., ethanol 95%, and the hydrophilic surfactant may be polysorbate 80. The resultant formulation includes stable micelles comprising nimodipine.

In another embodiment of the invention, the concentrate may be prepared by admixing a suitable amount of nimodipine to an organic solvent and the hydrophilic surfactant together for a sufficient period of time to form stable micelles. Thereafter, a suitable pharmaceutical medium for injection (e.g., water for injection) is added to prepare the final nimodipine concentrate formulation. In certain preferred embodiments, the organic solvent may be, e.g., polyethylene glycol, and the hydrophilic surfactant may be polysorbate 80. In certain embodiments of the present invention where an organic solvent is included, the organic solvent comprises at least 25% (and at least 40% in certain embodiments) of the formulation in injection concentrate and at least 1% in final diluted injection solution. In other preferred embodiments, the solvent comprises from about 10 to about 90%, and preferably from greater than 30% to about 90% by weight in injection concentrate and from about 0.1 to about 4% in final diluted injection solution.

In another embodiment of the invention, the concentrate may be prepared by admixing a suitable amount of nimodipine to a pharmaceutically acceptable oil carrier and a hydrophilic surfactant until a clear solution is obtained, and adding at least one pharmaceutically acceptable emulsifier to make a nano-emulsion and/or a self-emulsifying concentrate formulation. The self-emulsifying formulation forms a nano-emulsion once diluted with water for injection or any commonly available intravenous infusion solutions. In such embodiments, the nimodipine is preferably in the oil phase preferably soybean oil, medium chain glycerides, oleic acid, ethyl oleate with other pharmaceutical acceptable excipients either alone or in combination with emulsifiers and water for injection. In certain embodiments, the emulsifier may be, e.g., phospholipid Lipoid 80 and/or PEG 400. The median particle size of micelles or nano-emulsions ranges from about 0.5 nanometer to about 350 nanometers. In certain embodiments of the present invention where an oil carrier is included, the oil carrier comprises from about 1% to about 30% of the formulation in injection concentrate and from about 0.005% to about 3% of the final diluted injection solution. In other preferred embodiments, the oil comprises from about 5% to about 20% of the formulation, by weight in injection concentrate and from about 0.025% to about 2% in final diluted injection solution. The amount of emulsifier may comprise from about 1% to about 30% of the formulation in the injection concentrate and from about 0.005% to about 3% of the final diluted injection.

In yet another embodiment of the invention, a suitable amount of nimodipine together with the hydrophilic surfactant is admixed into a suitable amount of a cyclodextrin (e.g., beta-cyclodextrin) in water for a sufficient period of time to form a stable nimodipine inclusion complex. In such embodiments, the cyclodextrin preferably comprises from about 5% to about 45% of the formulation in injection concentrate and from about 0.025% to about 4.5% of the final diluted injection solution.

In certain embodiments of the present invention, the hydrophilic surfactant comprises at least about 8% of the formulation in the injection concentrate and at least 0.1% in the final diluted injection solution. In other preferred embodiments, the hydrophilic surfactant comprises from about 1% to about 15% of the formulation, by weight of the injection concentrate and from about 0.01% to about 2.5% of the final diluted injection solution.

In certain preferred embodiments, the hydrophilic surfactant comprises a pharmaceutically acceptable non-ionic surfactant. The non-ionic surfactant is preferably included in an amount sufficient to inhibit precipitation of drug substance from the pharmaceutically acceptable medium for injection (e.g., aqueous solution) after dilution. Non-ionic surfactants form stable micelles with drug substance, can solubilize the drug and may impart additional photo stability to the drug.

Using HLB values as a rough guide, hydrophilic surfactants are considered those compounds having an HLB value greater than 10 particularly from 12 to 17. The hydrophilic non-ionic surfactant is more soluble in water than in oil (having HLB higher than 10).

Pharmaceutically acceptable non-ionic surfactants useful in the formulations of the present invention include but are not limited to, for example, polyoxyethylene compounds, ethoxylated alcohols, ethoxylated esters, ethoxylated amides, polyoxypropylene compounds, propoxylated alcohols, ethoxylated/propoxylated block polymers, and propoxylated esters, alkanolamides, amine oxides, fatty acid esters of polyhydric alcohols, ethylene glycol esters, diethylene glycol esters, propylene glycol esters, glyceryl esters, polyglyceryl fatty acid esters, sorbitan esters, sucrose esters, and glucose (dextrose) esters. Further examples are reaction products of a natural or polyethoxylated castor oil and ethylene oxide. The ethoxylated castor oil may have an ethylene oxide content of 25 to 100 moles ethylene oxide per molecule, preferably 35 to 60 moles ethylene oxide per molecule. The natural or polyethoxylated castor oil may be reacted with ethylene oxide in a molar ratio of from about 1:35 to about 1:60, with optional removal of the polyethoxylated component from the products. Non-ionic hydrophilic surfactants useful in the present invention further include alkylgluceosides; alkylmaltosides; alkylthioglucosides; lauryl macrogolglycenides; polyoxyethylene alkyl ethers; polyoxyethylene alkylphenols; polyethylene glycol fatty (mono- and di-) acid esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene sterols and analogues thereof; polyoxyethylene vegetable oils, polyoxyethylene hydrogenated vegetable oils; reaction mixtures of polyols and at least one member selected from the group consisting of fatty acids, glycerides, vegetable oils, hydrogenated vegetable oils, in sterols; sugar esters, sugar ethers; sucroglycerides; fatty acid salts, bile salts, phospholipids, phosphoric acid esters, carboxylates, sulfates, sulfonates. More specifically, the nonionic surfactant may comprise, for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof. Although polyethylene glycol (PEG) itlf does not function as a surfactant, a variety of PEG-fatty acid esters have useful surfactant properties. Among the PEG-fatty acid monoesters, esters of lauric acid, oleic acid, and stearic acid are most useful.

Examples of the same include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. Polyethylene glycol fatty acid esters are also suitable for use as surfactants in the compositions of the present invention, such as PEG-20 dilaurate, PEG-20 dioleate, PEG-20 distearate, PEG-32 dilaurate, PEG-32 dioleate, PEG-20 glyceryl laurate, PEG-30 glyceryl laurate, PEG-40 glyceryl laurate, PEG-20 glyceryl oleate, and PEG-30 glyceryl oleate. The hydrophilic surfactant may further comprise mixtures of any of the foregoing.

Polysorbate 80, an especially preferred hydrophilic non-ionic surfactant in the formulations of the present invention, is a surfactant commonly used in protein parenteral formulations to minimize denaturation at the air-water interface. Polysorbate 80 is also sometimes used in injectable solution formulations of small molecules for the purpose of solubility enhancement due to micelle formation. Polysorbates are nonionic surfactants of sorbitan esters. Polysorbates useful in the present invention include, but are not limited to polysorbate 20, polysorbate 40, polysorbate 60, polysorbate 80 (Tween 80) and any combinations or mixtures thereof. Other suitable preferred surfactants includes poloxamer, poloxamer 407, transcutol. The surfactant can be any surfactant suitable for use in pharmaceutical compositions. Suitable surfactants can also be ionic hydrophilic surfactants or hydrophobic surfactants. Suitable hydrophilic surfactants can be anionic, cationic, zwitterionic or non-ionic, although non-ionic hydrophilic surfactants are presently preferred. Preferably, the nimodipine formulations of the invention include at least one non-ionic hydrophilic surfactant.

However, in other embodiments, the nimodipine formulations may include mixtures of two or more non-ionic hydrophilic surfactants, as well as mixtures containing at least one non-ionic hydrophilic surfactant and at least one hydrophobic surfactant.

In certain embodiments, the surfactant can be one or more of the surfactants described in U.S. Pat. No. 6,363,471, hereby incorporated by reference.

In certain embodiments of the present invention, the organic solvent is an alcohol (e.g., ethanol) and the solubilizer is polysorbate.

In the above embodiments, the nimodipine is solubilized using surface active agents as solubilizers via the formation of colloidal particles called micelles and stabilized by using co-solvents and/or appropriate substrates in the aqueous formulation. This results in the formation of micelles, or minute colloidal particles which surround the nimodipine molecule, isolating it from the water molecules surrounding it, but forming a clear aqueous solution. The liquid formulations are suitable for use as parenteral, nasal or oral administration.

Water-miscible surfactant molecules like polysorbate consists of both hydrophobic and hydrophilic portions that can solubilize select poorly water-soluble drugs. Surfactants can also self-assemble to form micelles once the surfactant monomer concentration reaches the critical micelle concentration. Thus, surfactants can solubilize drug molecules by either a direct co-solvent effect or by uptake into micelles. The non-ionic surfactants in commercially available solubilized oral and injectable formulations include polyoxyl 35 castor oil (Cremophor EL), polyoxyl 40 hydrogenated castor oil (Cremophor RH 40), polysorbate 20 (Tween 20), polysorbate 80 (Tween 80), d-tocopherol polyethylene glycol 1000 succinate (TPGS), Solutol HS-15, sorbitan monooleate (Span 80), polyoxyl 40 stearate, and various polyglycolyzed glycerides including Labrafil M-1944CS, Labrafil M-2125CS, Labrasol, Gellucire 44/14, and Softigen 767.

In the present invention nimodipine formulation preferably forms colloidal structures (micelles) about 10 nm in diameter. In other preferred embodiments, the mean diameter of the colloidal structures varies from about 0.5 nm to about 200 nm and more preferably about 5 nm to about 50 nm. In the present invention, the nimodipine micelle structure is thermally stable during a terminal sterilization process by autoclaving at 121° C. for 30 minutes.

In embodiments utilizing an oil carrier, the formulation may include, for example, an oil carrier sin the form of commercially available emulsions including Intralipid (10-20% soybean oil), Liposyn (10-20% safflower oil), and Lipofundid MCT/TCL (5-10% soybean oil and medium-chain triglycerides). The nimodipine is oil-soluble, and can be formulated for intravenous administration in an oil-in-water emulsion because the nimodipine partitions into the oil phase.

In certain preferred embodiments, the nimodipine injectable formulation is a cyclodextrin inclusion complex. Suitable cyclodextrins include but are not limited to a β-cyclodextrin such as hydroxy-propyl-β-cyclodextrin and a β-cyclodextrin comprising one or more hydroxybutyl sulfonate moieties such as sulfobutyl-ether-β-cyclodextrin, alpha-cyclodextrins, gamma-cyclodextrins, and cyclodextrins as described in U.S. Pat. No. 6,610,671 or 6,566,347 (both of which are incorporated by reference). In one embodiment, the nimodipine injectable formulation comprises a beta-cyclodextrin inclusion complex formed by the continuous mixing of nimodipine, hydrophilic surfactant and beta-cyclodextrin for 48 to 78 hours with occasional heating at about 60 degrees in a water bath to increase complex formation.

Any suitable pharmaceutically acceptable water-miscible organic solvent can be used in the present invention. Selection of a suitable organic solvent will depend in part upon the solubility of the active material (nimodipine) in the solvent, the degree to which the solvent is miscible in water, and the tolerability of the solvent. The solvent should be physiologically acceptable. Examples of solvents that may be used in the present invention include, but are not limited to, various alcohols such as ethanol, glycols, glycerin, propylene glycol, and various polyethylene glycols and dimethyl isosorbide (DMI). Additional useful alcohols include but are not limited to methanol (methyl alcohol), ethanol, (ethyl alcohol), 1-propanol (n-propyl alcohol), 2-propanol (isopropyl alcohol), 1-butanol (n-butyl alcohol), 2-butanol (sec-butyl alcohol), 2-methyl-1-propanol (isobutyl alcohol), 2-methyl-2-propanol (t-butyl alcohol), 1-pentanol (n-pentyl alcohol), 3-methyl-1-butanol (isopentyl alcohol), 2,2-dimethyl-1-propanol (neopentyl alcohol), cyclopentanol (cyclopentyl alcohol), 1-hexanol (n-hexanol), cyclohexanol (cyclohexyl alcohol), 1-heptanol (n-heptyl alcohol), 1-octanol (n-octyl alcohol), 1-nonanol (n-nonyl alcohol), 1-decanol (n-decyl alcohol), 2-propen-1-ol (allyl alcohol), phenylmethanol (benzyl alcohol), diphenylmethanol (diphenylcarbinol), triphenylmethanol (triphenylcarbinol), glycerin, phenol, 2-methoxyethanol, 2-ethoxyethanol, 3-ethoxy-1,2-propanediol, Di(ethylene glycol) methyl ether, 1,2-propanediol, 1,3-propanediol, 1,3-butanediol, 2,3-butanediol, 1,4-butanediol, 1,2-pentanediol, 1,3-pentanediol, 1,4-pentanediol, 1,5-pentanediol, 2,3-pentanediol, 2,4-pentanediol, 2,5-pentanediol, 3,4-, pentanediol, and 3,5-pentanediol.

In embodiments in which an emulsifier is incorporated into the concentrate, the emulsifier may be a pharmaceutically acceptable polyethylene glycol. Polyethylene glycol is available in many different grades having varying molecular weights. For example, polyethylene glycol is available as PEG 200; PEG 300; PEG 400; PEG 540 (blend); PEG 600; PEG 900; PEG 1000; PEG 1450; PEG 1540; PEG 2000; PEG 3000; PEG 3350; PEG 4000; PEG 4600 and PEG 8000. In certain embodiments the polyethylene glycol used to prepare the nimodipine concentrate is preferably PEG 400.

The nimodipine concentrates of the invention may be contained in any pharmaceutically acceptable container (e.g., ampules, vials) in a unit dose for later dilution (e.g., at the site and time of administration to a human patient).

Dilution

The injectable nimodipine formulations of the invention are preferably clear and contain the nimodipine in micelles or inclusion complexes, etc. which can be diluted with a pharmaceutically acceptable carrier for injection (e.g., water for injection) to produce a thermodynamically stable dispersion of non-ionic surfactant nanoparticles which are micelles, inclusion complexes, etc., as described and disclosed herein. The diluted nimodipine formulation is stable, i.e., the nimodipine does not phase separate across a broad range of temperatures at a wide range of water hardness and a wide range of pH. Thus, the nimodipine injection concentrate disclosed herein, when diluted with water for injection, saline, dextrose or commonly available infusion solutions up to a concentration of 0.01 mg/ml remains a clear solution and displays no precipitation of nimodipine.

In accordance with the present invention, the nimodipine formulation allows for administration of a single 250 ml infusion bag or bottle that contains IV nimodipine comprising, e.g., less than 2% or less than 1% w/v alcohol in a predominantly aqueous medium, a distinct improvement over IV Nimotop. This lower alcohol content in the formulation provides many advantages known to those skilled in the art, for example, making the inventive nimodipine formulation amenable for administration to patients suffering from alcoholism, impaired alcohol metabolism and those who are pregnant and breast feeding.

The present invention is a micellar formulation of nimodipine that provides for greatly enhanced aqueous solubility and stability including photo-stability. Nimodipine does not precipitate out of this formulation even when diluted with water up to 250 times its original concentration.

In certain embodiments of the present invention, the nimodipine injection concentrate is diluted in an infusion bag containing water for injection or any commonly available intravenous infusion solution. Infusion volumes can range from about 50 ml to about 1000 ml. The current invention provides for dilution of formulation in a single infusion bag and infused over a specific period unlike Bayer's Nimotop intravenous injection which requires a three-way stopcock auxiliary to infuse Nimotop solution along with two other co-infusion solutions to prevent any drug precipitation. The current invention provides for a single infusion solution that does not precipitate upon dilution and/or administration thus improving safety and efficacy.

In certain preferred embodiments, the nimodipine injection can be further diluted to a $2.5 \times 10^{-5}$ mole solution of nimodipine to rinse the exposed arteries after clipping the aneurysm and before an intravenous infusion of nimodipine administered to improve patient outcome.

In certain preferred embodiments, the novel solvent free (e.g., less than 1% w/v organic solvent such as ethanol) nimodipine formulation can be administered intravenous bolus, intravenous infusion, intra-arterial, intraoral, intranasal using a naso-gastric tube.

In certain preferred embodiments, the nimodipine injection after dilution with commonly available infusion solutions, the infusion set and bag can be covered with ultraviolet light (UV) protective bags to further protect it from photo-degradation.

The compounds of the invention may be administered parenterally in formulations eventually containing conventional non-toxic pharmaceutically acceptable carriers, adjuvants and vehicles as desired.

Injectable preparations, for example sterile injectable aqueous or oleaginous suspensions may be formulated according to known art using suitable dispersing or wetting agents and suspending agents. The sterile injectable preparation may also be a sterile injectable solution or suspension in a non-toxic parenterally acceptable diluent or solvent. Among the acceptable vehicles and solvents are water, Ringer's solution and isotonic sodium chloride. In addition, sterile, fixed oils are conventionally employed as a solvent or suspending medium. For this purpose any bland fixed oil may be employed including synthetic mono or diglycerides, in addition fatty acids such as oleic acid find use in the preparation of injectables. Suitable carriers for intravenous administration include physiological saline or phosphate buffered saline (PBS), and solutions containing solubilizing agents, such as glucose, polyethylene glycol, and polypropylene glycol and mixtures thereof.

The formulation may include an aqueous vehicle. Aqueous vehicles include, by way of example and without limitation, Sodium Chloride Injection, Ringers Injection, Isotonic Dextrose Injection, Sterile Water Injection, Dextrose, and Lactated Ringers Injection. Nonaqueous parenteral vehicles include, by way of example and without limitation, fixed oils of vegetable origin, cottonseed oil, corn oil, sesame oil and peanut oil.

Antimicrobial agents in bacteriostatic or fungistatic concentrations must be added to parenteral preparations packaged in multiple dose containers which include phenols or cresols, mercurials, benzyl alcohol, chlorobutanol, methyl and propyl p-hydroxybenzoic acid esters, thimerosal, benzalkonium chloride, benzethonium chloride, boric acid, p-hydroxybenzoates, phenols, chlorinated phenolic compounds, alcohols, quarternary compounds, mercurials, mixtures of the foregoing and the like. Isotonic agents include, by way of example and without limitation, sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80) [A sequestering or chelating agent of metal ions include EDTA.] Pharmaceutically acceptable pH adjusting agents include, by way of example and without limitation, sodium hydroxide, hydrochloric acid, citric acid or lactic acid. The nimodipine formulations of the invention may additionally include physiologically acceptable components such as sodium chloride and like materials conventionally used to achieve isotonicity with typical body fluids, pH buffers to establish a physiologically compatible pH range and to enhance the solubility of the nimodipine, preservatives, stabilizers and antioxidants and the like.

In certain preferred embodiments, the injectable formulations after dilution with water for injection and other commonly available intravenous infusion solutions, the pH of final diluted solution will be from about 3 to about 9, and in certain preferred embodiments from about 4.5 to about 8. In some embodiments of the present invention, the pH is adjusted using a pharmaceutically acceptable buffer or alkalizing agent, with suitable alkalizing agents and buffers including but not limited to NaOH, KOH, triethylamine, meglumine, L-Arginine, sodium phosphate buffer (either sodium phosphate tribasic, sodium phosphate dibasic, sodium phosphate monobasic, or o-phosphoric acid), sodium bicarbonate, and mixtures of any of the foregoing.

In certain other embodiments, the formulation may be made isotonic via the addition of a tonicity agent, such as but not limited to any pharmaceutically acceptable sugar, salt or any combinations or mixtures thereof, such as, but not limited to dextrose and sodium chloride. The tonicity agents may be present in an amount from about 100 mOsm/kg to about 500 mOsm/kg, or from about 200 mOsm/kg to about 400 mOsm/kg, or from about 280 mOsm/kg to about 320 mOsm/kg.

a. Treatment with Nimodipine

In accordance with the present invention, intravenous nimodipine solution can treat conditions such as, but not limited to, aneurysms, subarachnoid hemorrhage, vasospastic angina, Prinzmetal angina, stable angina, acute myocardial infarction, myocardial arrest, arrhythmia, systemic hypertension, pulmonary hypertension, congestive heart failure, coronary artery surgery and hypertrophic cardiomyopathy.

Nimodipine is indicated for the treatment of ischaemic neurological deficits following aneurysmal subarachnoid haemorrhage. With respect to Nimotop® 0.02% solution for infusion (Bayer plc), the recommended treatment is as follows: for the first two hours of treatment 1 mg of nimodipine, i.e. 5 ml Nimotop solution, (about 15 µg/kg bw/h), should be infused each hour via a central catheter. If it is well tolerated, the dose should be increased after two hours to 2 mg nimodipine, i.e. 10 ml Nimotop solution per hour (about 30 µg/kg bw/h), providing no severe decrease in blood pressure. Patients of body weight less than 70 kg or with unstable blood pressure should be started on a dose of 0.5 mg nimodipine per hour (2.5 ml of Nimotop solution), or less if necessary. Nimotop capsules are also available in the U.S. for oral administration, each one containing 30 mg of nimodipine in a vehicle of glycerin, peppermint oil, purified water and polyethylene glycol 400. The oral dose is 60 mg every 4 hours for 21 consecutive days, preferably not less than one hour before or two hours after meals.

In certain embodiments of the present invention, the IV nimodipine solution can be continuously infused over a period of about 3 weeks. The rate of infusion can be titrated based on patient tolerance and avoiding a decrease in blood pressure. The preferred infusion rate is from about 0.05 mg nimodipine per hour to about 5 mg nimodipine per hour. A dose titration is not possible with currently US FDA approved oral dosage forms.

In certain embodiments of the present invention, the IV nimodipine dose is reduced to about 2 to 10 mg every five hours compared to the current approved oral dose of 60 mg every four hours without reduction in drug product efficacy and safety. The current US FDA approved oral nimodipine drug product has high first-pass metabolism resulting in numerous metabolites, all of which are either inactive or considerably less active than the parent compound. The bioavailability of nimodipine averages 13% after oral administration. The first-pass metabolism is avoided via intravenous administration, and intra-subject (patient) variability associated with current approved oral dosage forms is reduced. Also, the single bag and or bottle continuous intravenous infusion of the nimodipine formulations of the invention is a convenient way to administer the effective concentration of nimodipine to unconscious patient and to patient having difficulty in swallowing oral dosage forms.

DETAILED DESCRIPTION OF PREFERRED EMBODIMENTS

The following examples of formulations in accordance with the present invention are not to be construed as limiting the present invention in any manner and are only samples of the various formulations described herein.

Examples 1-4

The formulation of Examples 1-4 were prepared as follows: nimodipine was added to ethanol while stirring and mixing until a clear solution is observed. Polysorbate 80 was then added as a surfactant while stirring and mixing for 30 minutes to form stable micelles. The volume was then increased to 5 ml with water for injection to prepare nimodipine injection concentrate formulations. The nimodipine injection concentrates can be diluted with any quantity of commonly used intravenous infusion solutions. The ingredients of Examples 1-4 are set forth in Table 1 below:

TABLE 1

| Composition | Quantity in mg | | | |
|---|---|---|---|---|
| | Ex.1 | Ex. 2 | Ex. 3 | Ex. 4 |
| Concentrated Injection Solution | | | | |
| Nimodipine | 10 | 10 | 10 | 10 |
| Ethanol 95% | 500 | 1000 | 2000 | 250 |
| Polysorbate 80 | 400 | 400 | 400 | 300 |
| Water for injection | qs 5 ml | qs 5 ml | qs 5 ml | qs 5 ml |
| Dilution (Continuous Intravenous Infusion Solution and or water for injection) | | | | |
| Nimodipine Concentrate | 5 ml | 5 ml | 5 ml | 5 ml |
| Infusion solution | 250 ml | 250 ml | 100 ml | 250 ml |

Example 5

The nimodipine formulation of Example 3 was tested in dilution studies performed with different commonly used intravenous infusion solutions (0.9% sodium chloride, 5% dextrose, and Lactated Ringer's solution) to understand the chemical interaction and to observe if nimodipine crystals precipitate after dilution. Nimodipine crystal precipitation was not observed following dilution of this formulation with these three different IV infusion solutions, as indicated in the Table 2 below.

TABLE 2

| Infusion solution | Dilution ratio | Nimodipine Conc, mg/ml | Nimodipine Assay,% | | | | | Observation |
|---|---|---|---|---|---|---|---|---|
| | | | Initial | 3 hour | 6 hour | 24 hour | 48 Hour | |
| 0.9% Sodium Chloride | 5 ml in 50 ml | 0.2 mg/ml | 102.0 | 101.3 | 101.8 | 102.7 | 101.7 | No precipitation observed |
| | 5 ml in 500 ml | 0.02 mg/ml | 99.0 | 105.3 | 103.6 | 102.3 | 101.9 | No precipitation observed |
| | 5 ml in 1000 ml | 0.01 mg/ml | 100.7 | 101.4 | 102.3 | 102.7 | 101.5 | No precipitation observed |
| 5% Dextrose | 5 ml in 50 ml | 0.2 mg/ml | 102.9 | 102.0 | 101.9 | 103.2 | 101.8 | No precipitation observed |
| | 5 ml in 500 ml | 0.02 mg/ml | 101.4 | 104.0 | 102.2 | 102.8 | 102.7 | No precipitation observed |
| | 5 ml in 1000 ml | 0.01 mg/ml | 100.8 | 104.0 | 103.8 | 102.2 | 101.9 | No precipitation observed |

TABLE 2-continued

| Infusion solution | Dilution ratio | Nimodipine Conc, mg/ml | Nimodipine Assay,% | | | | | Observation |
|---|---|---|---|---|---|---|---|---|
| | | | Initial | 3 hour | 6 hour | 24 hour | 48 Hour | |
| Lactated Ringer's | 5 ml in 50 ml | 0.2 mg/ml | 102.3 | 102.0 | 101.8 | 102.4 | 100.4 | No precipitation observed |
| | 5 ml in 500 ml | 0.02 mg/ml | 99.5 | 101.7 | 102.8 | 102.6 | 102.2 | No precipitation observed |
| | 5 ml in 1000 ml | 0.01 mg/ml | 100.2 | 101.7 | 102.5 | 102.2 | 102.1 | No precipitation observed |

FIG. 1 is a graphical representation of the nimodipine concentration of the formulation of Example 3 at the tested concentrations (0.2 mg/ml, 0.02 mg/ml and 0.01 mg/ml) in 0.9% sodium chloride solution.

Figure 2:
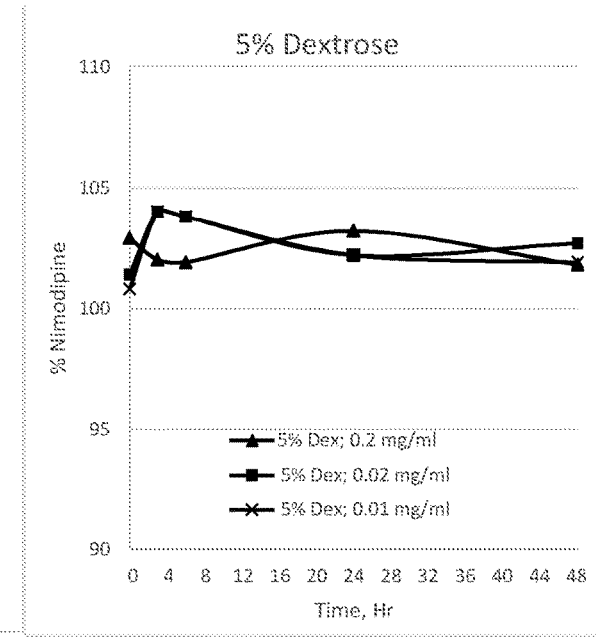
FIG. 2 is a graphical representation of the nimodipine concentration of the formulation of Example 3 at the tested concentrations (0.2 mg/ml, 0.02 mg/ml and 0.01 mg/ml) in 5% dextrose solution.

FIG. 2 is a graphical representation of the nimodipine concentration of the formulation of Example 3 at the tested concentrations (0.2 mg/ml, 0.02 mg/ml and 0.01 mg/ml) in 5% dextrose solution.

Figure 3:
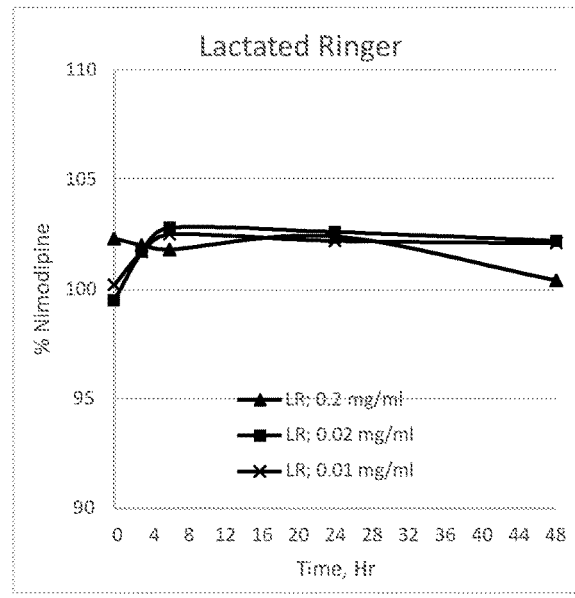
FIG. 3 is a graphical representation of the nimodipine concentration of the formulation of Example 3 at the tested concentrations (0.2 mg/ml, 0.02 mg/ml and 0.01 mg/ml) in Lactated Ringer's solution.

FIG. 3 is a graphical representation of the nimodipine concentration of the formulation of Example 3 at the tested concentrations (0.2 mg/ml, 0.02 mg/ml and 0.01 mg/ml) in Lactated Ringer's solution.

The concentrate formulation of Example 3 was also exposed to UV light under controlled UV camber for 48 hours to understand the photo degradation of this novel nimodipine formulation. The nimodipine formulation was kept in amber color and clear glass vial under the same condition. As shown in Table 3 below, no photo degradation was observed in both amber and clear glass vials. This result supports the conclusion that the concentrate (micelle) formulation of Example 3 provides photo-stability to nimodipine.

TABLE 3

| Duration of UV light Exposure | Amber Color Vial 2 mg/ml | Clear Glass Vial 2 mg/ml | Observation |
|---|---|---|---|
| Initial | 103.1 | 103.1 | No precipitation observed |
| 3 Hour | 103.5 | 98.8 | No precipitation observed |
| 6 Hour | 101.2 | 102.7 | No precipitation observed |
| 24 Hour | 103.4 | 103.5 | No precipitation observed |
| 48 Hour | 102.9 | 98.7 | No precipitation observed |

Figure 4:
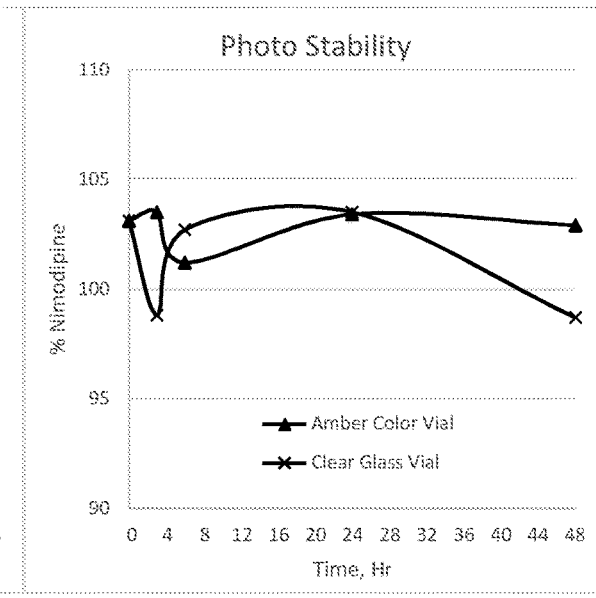
FIG. 4 is a graphical representation of the concentration of the nimodipine formulation of Example 3 over time, where the formulation is at a nimodipine concentration of 2 mg/ml and contained in an amber colored vial and in a clear glass vial and exposed to UV light.

FIG. 4 is a graphical representation of the duration of UV light exposure of the nimodipine formulation of Example 3 where the formulation is at a nimodipine concentration of 2 mg/ml and contained in an amber colored vial and in a clear glass vial. The plot shows the nimodipine concentration over time.

Examples 6-8

In Examples 6-8, a nimodipine concentrate is prepared as follows: Add nimodipine to polysorbate 80 and polyethylene glycol 400 while stirring and mix for 30 minutes to form stable micelles and make the volume up to 5 ml with water for injection. Benzyl alcohol added as preservative. This nimodipine injection concentrate can be diluted with any quantity of commonly used intravenous infusion solutions. The formulations of Examples 6-8 are set forth in more detail in Table 4 below:

TABLE 4

| Composition | Quantity in mg | | |
|---|---|---|---|
| | Ex. 6 | Ex. 7 | Ex. 8 |
| Concentrated Injection Solution | | | |
| Nimodipine | 10.5 | 10.5 | 10.5 |
| Polysorbate 80 | 400 | 400 | 1050 |
| PEG 400 | 500 | | |
| Benzyl Alcohol | 100 | 100 | 100 |
| Water for injection | qs 5 ml | qs 5 ml | qs 5 ml |
| Dilution (Continuous Intravenous Infusion Solution) | | | |
| Nimodipine Concentrate | 5 ml | 5 ml | 5 ml |
| Infusion solution | 50 ml | 50 ml | 50 ml |

Examples 9-11

In Examples 9-11, a nimodipine concentrate is prepared as follows: Add nimodipine to polysorbate 80 and soybean oil while stirring and mix till clear solution is observed and Phospholipid Lipoid 80 and PEG 400 as emulsifiers to make a nano-emulsion and/or self emulsifying formulation. This nimodipine injection concentrate can be diluted with any quantity of commonly used intravenous infusion solution to form nano-emulsions. The formulations of Examples 9-11 are set forth in more detail in Table 5 below:

TABLE 5

| Composition | Quantity in mg | | |
|---|---|---|---|
| | Ex. 9 | Ex. 10 | Ex. 11 |
| Concentrated Injection Solution | | | |
| Nimodipine | 10 | 10 | 10 |
| Polysorbate 80 | 600 | 1725 | 2600 |
| Soybean Oil | 50 | 850 | 990 |
| Phospholipid Lipoid 80 | 12.5 | | |
| PEG 400 | | 2415 | 1400 |
| Dilution (Continuous Intravenous Infusion Solution) | | | |
| Nimodipine Concentrate | 672.5 mg | 5 gm | 5 gm |
| Infusion solution | 50 ml | 50 ml | 50 ml |

Example 12

In Example 12, a nimodipine concentrate is prepared as follows: Add beta-cyclodextrin to water for injection while stirring and mix for 15 minutes and add nimodipine and polysorbate 80 while stirring to above dispersion and mix for 48 hours to get clear solution. Heating was applied using a water bath heated up to 60 degrees to increase the rate of inclusion complex.

The formulation of Example 12 is set forth in more detail in Table 6 below:

TABLE 6

| Composition | Quantity in mg |
|---|---|
| Concentrated Injection Solution | |
| Nimodipine | 10.5 |
| Polysorbate 80 | 400 |
| Beta cyclodextrin | 1500 |
| Water for injection | qs 5 ml |
| Dilution (Continuous Intravenous Infusion Solution) | |
| Nimodipine Concentrate | 5 ml |
| Infusion solution | 50 ml |

Example 13

Figure 5:
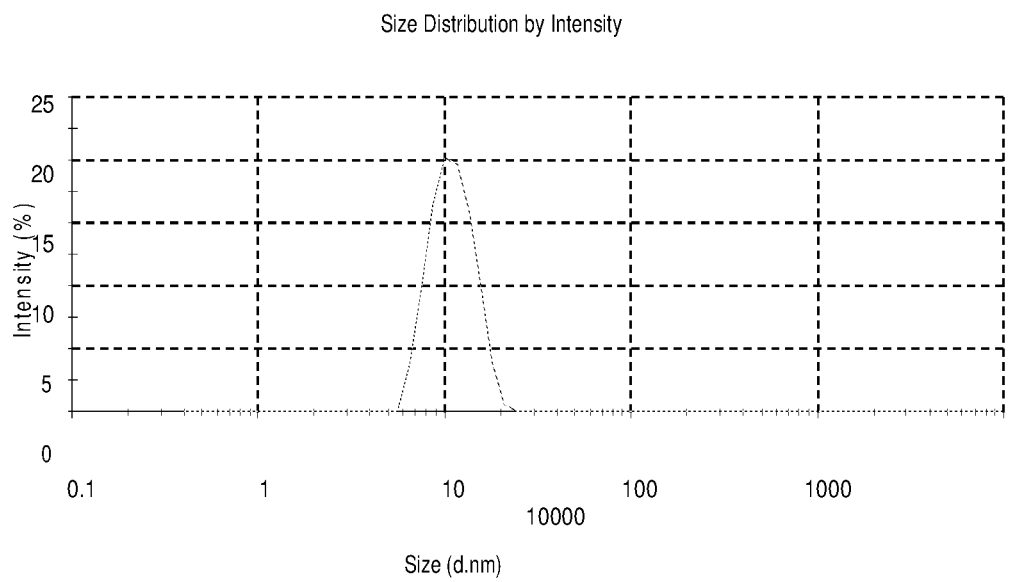
FIG. 5 is a graphical representation of the micelle distribution of Example 3 prior to terminal sterilization.
Figure 6:
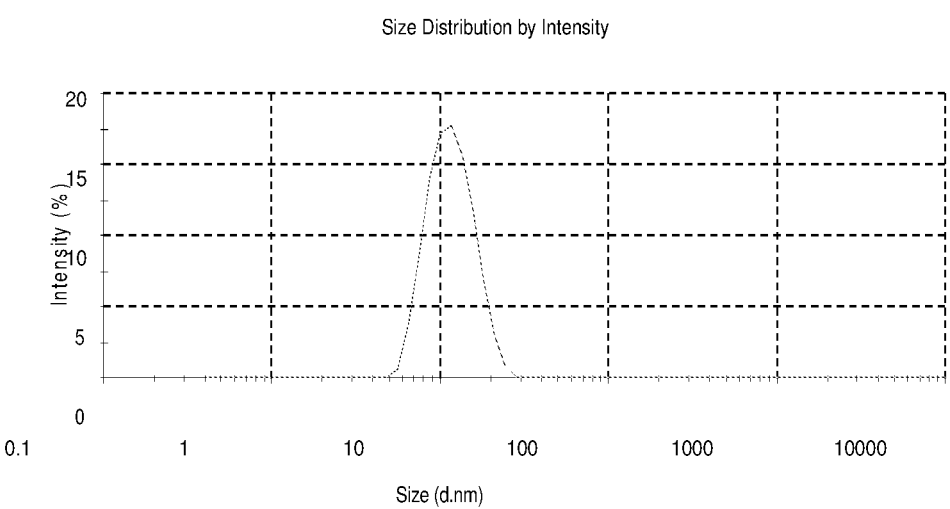
FIG. 6 is a graphical representation of the micelle distribution of Example 3 after terminal sterilization.

In Example 13, the nimodipine concentrate of Example 3 is subjected to a terminal sterilization process by autoclaving at 121° C. for 30 minutes. FIG. 5 is a graph showing micelle size distribution of Example 3 before terminal sterilization with a peak at a particle size diameter of approximately 10 nm. The size distribution was measured using a Malvern Zetasizer Nano ZS at a temperature of 25° C. FIG. 6 is a graph showing micelle size distribution of Example 3 after terminal sterilization (autoclaved at 121° C. for 30 minutes) with a peak at a particle size diameter of approximately 10 nm. Size distribution was measured using a Malvern Zetasizer Nano ZS at a temperature of 25° C. Based on these results, the formulation of Example 3 is considered to be stable.

Example 14

The formulation of Example 14 was prepared as follows: nimodipine was added to ethanol while stirring and mixing until a clear solution is observed. Polysorbate 80 was then added as a surfactant while stirring and mixing for 30 minutes to form stable micelles. Sufficient water for injection was then added to the solution to generate 5 ml of nimodipine injection concentrate. The nimodipine injection concentrate can be further diluted with any amount of commonly used intravenous infusion solutions. The ingredients of Examples 14 are set forth in Table 7 below:

TABLE 7

| Concentrated Injection Solution | |
|---|---|
| Composition | Quantity in mg |
| Nimodipine | 10 |
| Dehydrated Alcohol | 1900 |
| Polysorbate 80 | 400 |
| Water for injection | qs 5 ml |

Example 15 (Stability)

Amber glass bottles were filled with the formulations of Example 3 (5 mL concentrate), Example 3 (100 mL ready to infuse) and Example 14 (5 mL concentrate) with a rubber stopper and flip-off seal and subjected to stability studies under the following conditions:

ICH accelerated conditions at 40° C.±2° C./75% RH±5% RH; and

ICH room temperature conditions at 25° C.±2° C./60% RH±5% RH

Samples were analyzed to measure the Nimodipine assay, impurities. Also physical stability of the invented formulation example physical appearance and pH drift was recorded. The stability of the concentrate of Example 3 is provided in Table 8 below.

TABLE 8

| | | | 40° C. ± 2° C./75% RH ± 5% RH | | | | 25° C. ± 2° C./60% RH ± 5% RH | | | | |
|---|---|---|---|---|---|---|---|---|---|---|---|
| Test | Specification | Initial | 1 Month | 2 Month | 3 Month | 6 Month | 1 Month | 2 Month | 3 Month | 6 Month | 9 Month |
| Description | light yellow or yellow liquid, free of particulate matter | Conforms | Y | Y | Y | Y | Y | Y | Y | Y | Y |
| pH | 4.0-9.0 | 5.5 | 5.5 | 5.5 | 5.5 | 5.5 | 5.5 | 5.5 | 5.5 | 5.5 | 5.5 |
| Assay by HPLC | 90.0% to 110.0% | 102.1% | 102.1% | 103.8% | 104.6% | 103.9% | 102.2% | 103.9% | 104.5% | 104.3% | 105.8% |
| Related substances (by HPLC) | | | | | | | | | | | |
| Nimodipine nitrophenyl pyridine analog | NMT 0.5% | ND | ND | 0.06 | 0.11 | 0.30 | ND | ND | 0.03 | 0.04 | 0.11 |
| Any unknown impurity | NMT 0.5% | | ND | ND | 0.04 | ND | ND | ND | 0.05 | ND | ND |
| Total impurities | NMT 2.0% | | | 0.06 | 0.15 | 0.30 | | | 0.08 | 0.04 | 0.11 |

ND Not Detected;
Y Conforms

The stability of ready-to-infuse embodiment of Example 3 is provided in Table 9 below.

TABLE 9

Stability data of Example 3 Ready-to-infuse (100 ml amber color vial)

| | | | 25° C. ± 2° C./60% RH ± 5% RH | | | | |
|---|---|---|---|---|---|---|---|
| Test | Specification | Initial | 1 Month | 2 Month | 3 Month | 6 Month | 9 Month |
| Description | light yellow or yellow liquid, free of particulate matter | Conforms | Y | Y | Y | Y | Y |
| pH | 4.0-9.0 | 5.5 | 5. | 5.5 | 5.5 | 5.5 | 5.5 |
| Assay by HPLC | 90.0% to 110.0% | 103.4% | 102.1% | 104.8% | 102.4% | 99.7% | 100.0% |
| Related substances (by HPLC) | | | | | | | |
| Nimodipine nitrophenyl pyridine analog | NMT | 0.08 | 0.20 | 0.26 | 0.11 | 0.42 | 0.29 |
| Any unknown impurity | 0.5% | ND | ND | ND | ND | ND | ND |
| Total impurities | NMT | 0.08 | | 0.26 | 0.11 | 0.42 | 0.29 |

ND Not Detected;
Y Conforms

The stability of the concentrate of Example 14 is provided in Table 10 below:

TABLE 10

Stability data of Example 14 Concentrate (5 ml amber color vial)

| | | | 40° C. ± 2° C./75% RH ± 5% RH | | | | 25° C. ± 2° C./60% RH ± 5% RH | | | |
|---|---|---|---|---|---|---|---|---|---|---|
| Test | Specification | Initial | 1 Month | 2 Month | 3 Month | 6 Month | 1 Month | 2 Month | 3 Month | 6 Month |
| Description | light yellow or yellow liquid, free of particulate matter | Conforms | Y | Y | Y | Y | Y | Y | Y | Y |
| pH | 4.0-9.0 | 5.5 | 5.5 | 5.5 | 5.5 | 5.5 | 5.5 | 5.5 | 5.5 | 5.5 |
| Assay by HPLC | 90.0% to 110.0% | 101.0% | 100.5% | 99.6% | 100.1% | 98.4% | 101.4% | 99.6% | 98.5% | 99.0% |
| Related substances (by HPLC) | | | | | | | | | | |
| Nimodipine nitrophenyl pyridine analog | NMT 0.5% | ND | ND | ND | 0.02 | ND | ND | ND | ND | ND |
| Any unknown impurity | NMT 0.5% | ND | ND | ND | ND | ND | ND | ND | ND | ND |
| Total impurities | NMT 2.0% | ND | ND | ND | 0.02 | ND | ND | ND | ND | ND |

ND Not Detected; Y Conforms

Example 16 (In-Vivo Study)

An in-vivo study was performed in healthy Wistar rats to evaluate drug release from a nimodipine continuous intravenous infusion made in accordance with Example 14. A single dose parallel study was conducted to evaluate the plasma and CSF (cerebral spinal fluid) pharmacokinetics and relative bioavailability of 0.73 mg nimodipine single intravenous infusion (for 4 hour) vs 5.5 mg of nimodipine oral solution (Nymalize). The pharmacokinetics study was performed in 6 healthy rats (3 males and 3 females). The test formulation was a single 0.73 mg dose (concentration of 0.182 mg/ml after dilution with D5W infusion solution) of nimodipine administered as a continuous intravenous infusion at a controlled rate over a period of 4 hours (continuous infusion). The reference product was a nimodipine 5.5 mg oral solution Nymalize (the oral bioavailability of nimodipine averages 13% and hence oral dose was adjusted accordingly) administered orally with the help of oral gavage. Blood samples were collected at 15 minutes, 30 minutes, and at 1, 2, 4, 6, 8, 12 and 24 hours post-dose. CSF samples were collected at 1, 2, 4, and 24 hours post-dose. All samples were analyzed using a validated analytical LC-MS method.

TABLE 11

| Treatment | Dose (mg/ rat) | Route of Administration | Formulation strength (mg/mL) | Infusion rate (mL/hour) | Dose volume (mL/rat) |
|---|---|---|---|---|---|
| IV infusion Example 14 | 0.73 | IV infusion | Concentrate: 2 mg/mL | 1.0 mL/hour | 4 mL/Rat |
| Nimodipine (oral) Nymalize | 5.50 | Oral | After Dilution: 0.182 mg/ml 3 mg/mL | NA | 1.83 mL by oral |

Following administration of a single dose of 0.73 mg over 4 hours by continuous infusion, the mean $C_{max}$ was found to be 249 ng/mL at a median $T_{max}$ of 1.92 hr. The mean $AUC_{0-t}$ and $AUC_{0-infinity}$ was found to be 1081 and 1084 ng*hr/mL, respectively. The mean elimination half-life was found to be 3.68 hr. The clearance and volume of distribution were 11.4 mL/min and 3.66 L, respectively.

Following administration of a single dose of 5.5 mg oral solution dose, the mean $C_{max}$ was found to be 479 ng/mL at a median Tmax of 0.75 hr. The $AUC_{0-t}$ and $AUC_{0-infinity}$ was found to be 1850 and 1850 ng*hr/mL, respectively. The mean elimination half-life was found to be 2.6 hr. The relative bioavailability was found to be 22.6% relative to intravenous continuous infusion test product.

Figure 7:
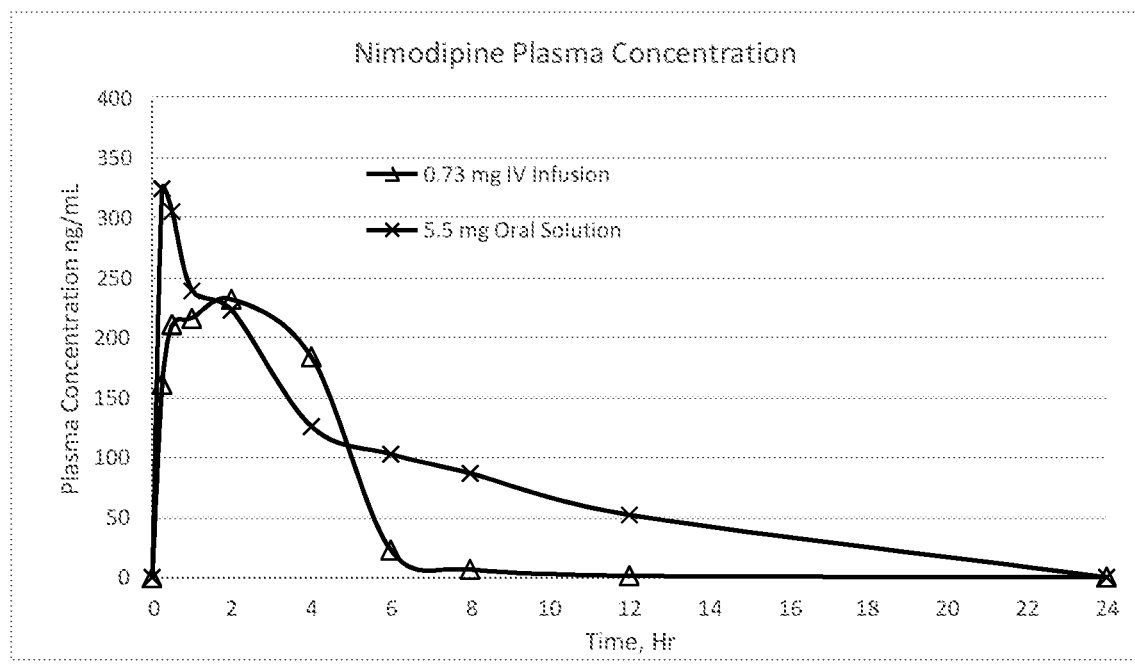
FIG. 7 is a graphical representation of the mean plasma concentration-time profile of nimodipine following reference (oral solution) and intravenous continuous infusion of test product (Example 14) in rats.

The pharmacokinetic results are reported in Table 12, 13 and FIG. 7 [mean plasma concentration-time profile of nimodipine following reference (oral solution) and intravenous continuous infusion of test product (Example 14) in rats].

TABLE 12 pharmacokinetic results of nimodipine continuous infusion

| Treatment/ Lot Number/ ROA | Rat Id | $T_{max}$ (hr) | $C_{max}$ (ng/mL) | $AUC_{last}$ (hr*ng/mL) | $AUC_{INF\_obs}$ (hr*ng/mL) | $t_{1/2}$ (hr) | Vz_obs (L) | Cl_obs (mL/min) |
|---|---|---|---|---|---|---|---|---|
| Nimodipine/ Example 14/ IV Infusion | 10 F | 1.00 | 240 | 1020 | 1020 | 1.96 | 2.02 | 11.9 |
| | 11 M | 2.00 | 246 | 1030 | 1040 | 4.10 | 4.17 | 11.8 |
| | 12 F | 4.00 | 269 | 1230 | 1230 | 3.30 | 2.83 | 9.9 |
| | 13 M | 0.50 | 212 | 923 | 925 | 4.48 | 5.10 | 13.2 |
| | 14 F | 2.00 | 262 | 1260 | 1260 | 3.15 | 2.63 | 9.6 |
| | 15 M | 2.00 | 263 | 1020 | 1030 | 5.08 | 5.20 | 11.8 |
| | Mean | 1.92 | 249 | 1081 | 1084 | 3.68 | 3.66 | 11.4 |
| | SD | 1.20 | 21 | 133 | 132 | 1.11 | 1.35 | 1.3 |
| | CV % | 62.60 | 8.50 | 12.30 | 12.20 | 30.10 | 37.00 | 11.8 |

TABLE 13 pharmacokinetic results of nimodipine oral solution

| Treatment/ Lot Number/ ROA | Rat Id | $T_{max}$ (hr) | $C_{max}$ (ng/mL) | $AUC_{last}$ (hr*ng/mL) | $AUC_{INF\_obs}$ (hr*ng/mL) | $t_{1/2}$ (hr) | Absolute Bioavailability (F %) |
|---|---|---|---|---|---|---|---|
| Nimodipine/ F0847/Oral | 25 F | 0.25 | 885 | 1700 | 1710 | 4.1 | 20.9 |
| | 26 M | 0.50 | 384 | 367 | 374 | NC | 4.6 |
| | 27 F | 2.00 | 516 | 6020 | 6020 | 1.7 | 73.7 |
| | 28 M | 0.50 | 85 | 306 | 307 | 3.1 | 3.8 |
| | 29 F | 1.00 | 897 | 2260 | 2260 | 1.9 | 27.7 |
| | 30 M | 0.25 | 106 | 422 | 423 | 2.4 | 5.2 |
| | Mean | 0.75 | 479 | 1850 | 1850 | 2.6 | 23 |
| | SD | 0.67 | 359 | 2200 | 2200 | 0.9 | 27 |
| | CV % | 89.4 | 75.0 | 119.2 | 119.0 | 35.8 | 119 |

TABLE 14

Plasma and CSF concentrations of nimodipine in rats treated with the nimodipine intravenous continuous infusion formulation of Example 14

| Route | Time (hr) | Plasma (ng/mL) | CSF (ng/mL) | CSF/ Plasma ratio |
|---|---|---|---|---|
| IV infusion for 4 hours (0.73 mg/rat) | 1 | 249 ± 118 | 1.56 ± 0.674 | 0.0064 ± 0.0010 |
| | 2 | 180 ± 16 | 1.26 ± 0.248 | 0.0070 ± 0.0017 |
| | 4 | 208 ± 52 | 1.52 ± 0.104 | 0.0075 ± 0.0013 |
| | 24 | 0.66 ± 0.65 | 0 | 0 |

Figure 8:
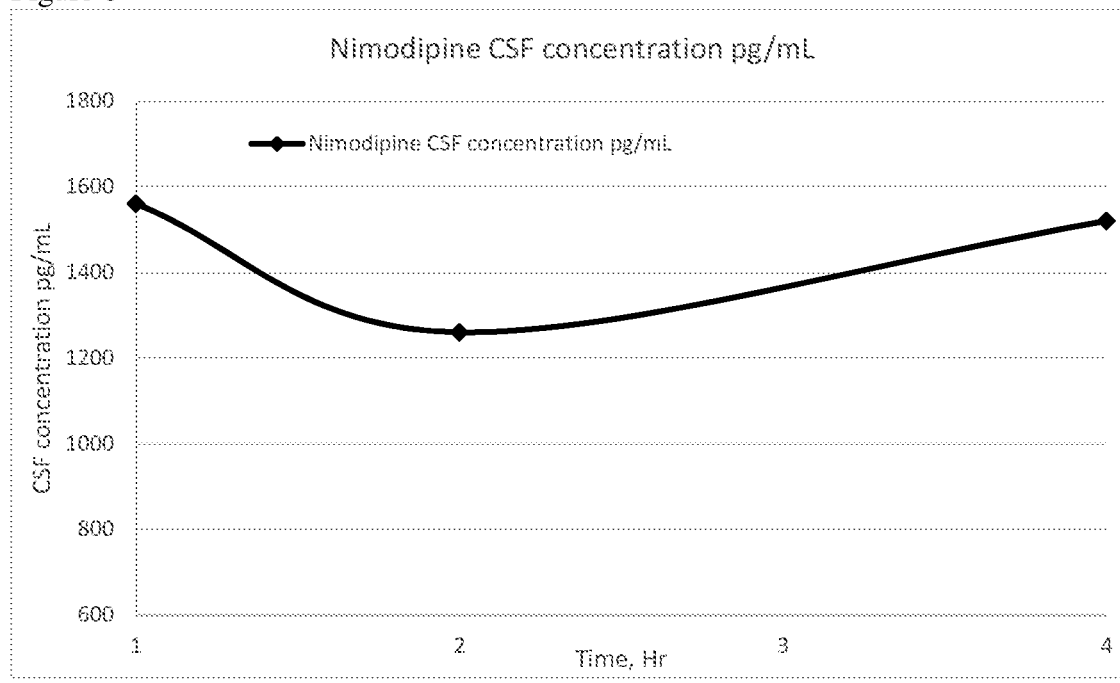
FIG. 8 is a graphical representation of the mean CSF concentrations of nimodipine in rats treated with nimodipine intravenous continuous infusion formulation.

Consistent levels of nimodipine was observed in the CSF over the duration of infusion of a single dose of 0.73 mg administered over 4 hours. The range of nimodipine CSF levels was measured at 1.26-1.56 ng/ml. Consistent nimodipine CSF concentrations were achieved within 1 hour of infusion. The CSF/Plasma ratio was found to be consistent up to 4 hours of infusion with ranges between 0.0064-0.0075. Plasma and CSF concentrations of nimodipine in rats treated with nimodipine intravenous continuous infusion formulation are reported in Table 14 and FIG. 8.

Because of high first-pass metabolism, the oral bioavailability of nimodipine averages 22% in this study. During the oral treatment period, the plasma concentrations and the shape of the concentration curve varied considerably between rats, probably reflecting variability in the first pass elimination, which also reflects the low mean oral bioavailability of nimodipine.

Figure 9:
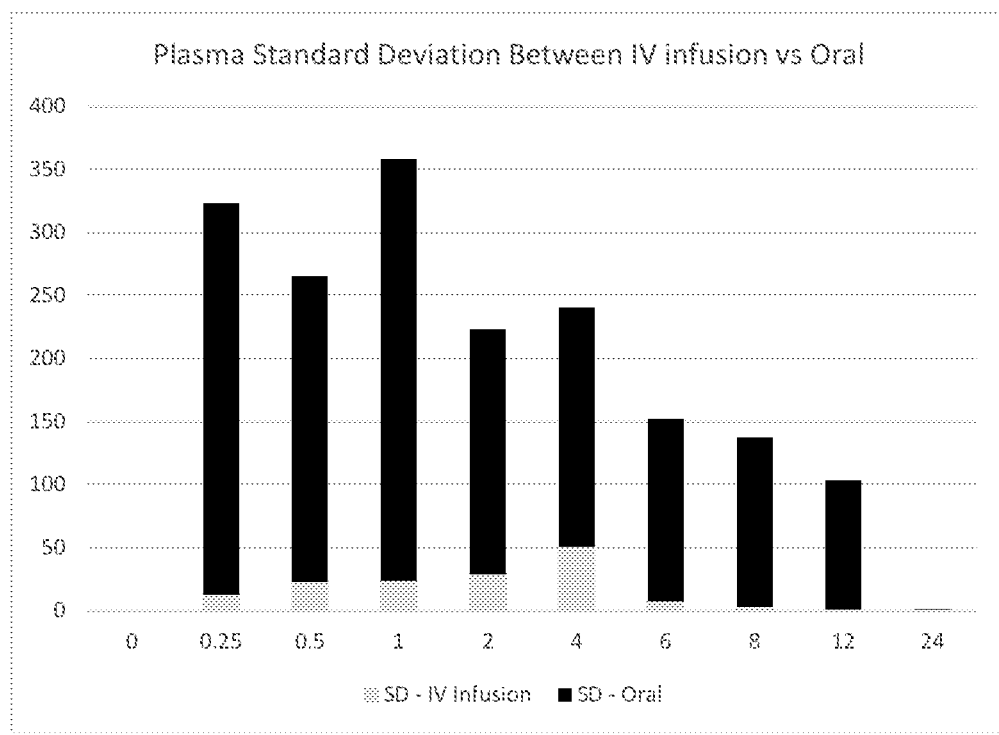
FIG. 9 is a graphical representation of the plasma concentrations standard deviation (SD) of nimodipine in rats when treated with nimodipine intravenous continuous infusion and reference oral solution.

The absolute bioavailability of continuous intravenous infusion nimodipine is 100%. The increased bioavailability of the IV infusion formulation also results in decreased pharmacokinetic variability. In addition, the avoidance of a first pass effect following intravenous infusion has the potential to decrease the impact of drug-drug interactions associated with CYP3A4 induction or inhibition. Plasma concentrations standard deviation (SD) of nimodipine in rats when treated with nimodipine intravenous continuous infusion and reference oral solution are reported in Table 15 and FIG. 9.

TABLE 15

| | Plasma Concentration Standard Deviation | |
|---|---|---|
| Time | Test—IV Infusion | Reference—Oral Solution |
| 0 | 0 | 0 |
| 0.25 | 13 | 310 |
| 0.5 | 23 | 242 |
| 1 | 24 | 334 |
| 2 | 29 | 194 |
| 4 | 51 | 189 |
| 6 | 7.8 | 144 |
| 8 | 2.89 | 134 |
| 12 | 0.14 | 103 |
| 24 | 0.65 | 0.42 |

It can be concluded that when the stable micellar nimodipine formulation of the invention is administered as a continuous intravenous infusion, first pass metabolism by the liver is minimized and resulting in improved bioavailability. Consistent levels of nimodipine are therefore maintained in plasma and CSF.

CONCLUSION

It will be apparent to those skilled in the art that the nimodipine concentrate and diluted formulations may be made using different but equivalent methods, and that these formulations may use other surfactants, carriers and emulsifiers beyond those specifically mentioned herein. Such obvious modifications are considered to be within the scope of the appended claims.

The invention claimed is:

1. A nimodipine injection concentrate formulation, comprising nimodipine base or a pharmaceutically acceptable nimodipine salt in a concentration from about 0.01 to about 5 mg/ml; an organic solvent consisting of ethanol; a pharmaceutically acceptable aqueous carrier; an optional preservative; and an effective amount of a single hydrophilic surfactant which is polysorbate 80 and the polysorbate 80 is from about 6% to about 10% of the injection concentrate formulation, such that nimodipine in the injection concentrate formulation is contained in micelles and the formulation is stable and clear, wherein the nimodipine injection concentrate formulation does not contain poloxamer, a phospholipid, or polyoxyethylene castor oil derivatives.

2. The nimodipine injection concentrate formulation of claim 1, comprising nimodipine base or a pharmaceutically acceptable nimodipine salt in a concentration from about 0.5 mg/ml to about 5 mg/ml, from about 1% to about 30% of the single hydrophilic surfactant, from about 30% to about 90% organic solvent; and from about 30 to about 70% of a pharmaceutically acceptable aqueous carrier comprising water for injection.

3. The nimodipine injection concentration formulation of claim 1, wherein the total volume of the concentrate formulation is from about 1 ml to about 10 ml.

4. The nimodipine injection concentrate formulation of claim 1, wherein the single hydrophilic surfactant is polysorbate 80 and the polysorbate 80 is from about 1% to about 15% of the injection concentrate formulation.

5. The nimodipine injection concentrate formulation of claim 1, wherein the single hydrophilic surfactant is polysorbate 80 and the polysorbate 80 is from about 6% to about 10% of the injection concentrate formulation.

6. The nimodipine injection concentrate formulation of claim 1, wherein the organic solvent comprises ethanol.

7. The nimodipine injection concentrate formulation of claim 1, wherein the nimodipine injection concentrate when diluted with a carrier selected from the group consisting sodium chloride injection, Ringers injection, isotonic dextrose injection, sterile water for injection, dextrose, Lactated Ringers injection, and total parenteral nutrition (TPN) to a concentration as dilute as 0.01 mg/ml nimodipine remains clear and displays no precipitation of nimodipine.

8. The nimodipine injection concentrate formulation of claim 1, wherein the nimodipine injection concentrate when diluted with a pharmaceutically acceptable aqueous injection medium allows for administration of a single 250 ml infusion bag or bottle that contains less than 2% w/v alcohol, the diluted injection medium remaining a clear micellar solution that displays no precipitation of nimodipine.

9. The nimodipine injection concentrate formulation of claim 1, which includes an effective amount of a preservative selected from the group consisting of cresols, mercurials, benzyl alcohol, chlorobutanol, methyl and propyl p-hydroxybenzoic acid esters, thimerosal, benzalkonium chloride, benzethonium chloride, boric acid, p-hydroxybenzoates, phenols, chlorinated phenolic compounds, alcohols, quaternary compounds, mercurials, and mixtures of any of the foregoing.

10. The nimodipine injection concentrate formulation of claim 1, which is diluted to a volume from about 50 ml to about 1000 ml with a pharmaceutical acceptable carrier for injection such that the nimodipine is present in a concentration from about 0.01 mg/ml to about 1.0 mg/ml, and the organic solvent is less than 2% w/v of the formulation, the nimodipine being substantially present in the form of micelles, the diluted formulation remaining clear micellar solution and displaying no crystal precipitation of nimodipine.

11. The nimodipine injection concentrate formulation of claim 1, wherein the median particle size of micelles containing nimodipine ranges from about 0.5 nanometer to about 350 nanometers.

12. The nimodipine injection concentrate formulation of claim 10, wherein the median particle size of micelles containing nimodipine ranges from about 0.5 nanometer to about 350 nanometers.

13. A method of treating a human patient having a condition selected from the group consisting of an aneurysm, subarachnoid hemorrhage, vasospastic angina, Prinzmetal angina, stable angina, acute myocardial infarction, myocardial arrest, arrhythmia, systemic hypertension, pulmonary hypertension, congestive heart failure, coronary artery surgery and hypertrophic cardiomyopathy, comprising continuously infusing in the human patient an intravenous solution comprising the nimodipine injection concentrate formulation of claim 1 over a period of about three weeks.

14. The method of claim 13, wherein the nimodipine infusion rate is from about 0.05 mg nimodipine per hour to about 5 mg nimodipine per hour.

15. The method of claim 13, wherein the intravenous nimodipine dose is from about 2 to 10 mg administered every five hours.

16. The nimodipine injection concentrate formulation of claim 1, which is prepared by mixing the nimodipine base or a pharmaceutically acceptable nimodipine salt with the organic solvent; adding the hydrophilic surfactant to the mixture of nimodipine and organic solvent; and thereafter adding from about 0.5 ml to about 4 ml of a pharmaceutically acceptable aqueous medium for injection to prepare a nimodipine concentrate formulation wherein nimodipine is contained in micelles.

17. The nimodipine formulation of claim 10, wherein the single hydrophilic surfactant is from about 0.01 to about 2.5% of the formulation.

18. The nimodipine formulation of claim 10, wherein the organic solvent is less than 1% of the formulation.

19. The nimodipine formulation of claim 10, which has a pH from about 4.5 to about 8.

20. The nimodipine injection concentrate formulation of claim 1, which is stable when exposed to conditions of 40° ° C.±2° C./75% RH±5% RH for at least 3 months; or which is stable when exposed to conditions of 25° C.±2° C./60% RH±5% RH for at least 12 months.

21. A directly infusible nimodipine formulation suitable for parenteral administration in humans, comprising nimodipine in a concentration from about 0.01 mg/ml to about 1.0 mg/ml, a pharmaceutically acceptable organic solventconsisting of ethanol copmrising less than 2% w/v of the formulation, a pharmaceutically acceptable aqueous carrier, and an effective amount of a single hydrophilic surfactant which is polysorbate 80 and is from 0.01% to about 2.5% w/v of the formulation, such that the nimodipine is substantially contained in micelles, the formulation comprising a volume from about 50 ml to about 1000 ml and contained in a pharmaceutically acceptable container, the formulation being a stable clear micellar solution and displaying no precipitation of nimodipine, wherein the directly infusible nimodipine injection formulation does not contain poloxamer, a phospholipid, or an oil.

22. The directly infusible nimodipine formulation of claim 21, wherein the single hydrophilic surfactant is from 0.01% to about 2.5% w/v of the formulation.

23. The directly infusible nimodipine formulation of claim 21, wherein the single hydrophilic surfactant is polysorbate 80 and the organic solvent comprises ethanol.

24. The directly infusible nimodipine injection formulation of claim 21, wherein the median particle size of micelles containing nimodipine ranges from about 0.5 nanometer to about 350 nanometers.

25. The directly infusible nimodipine injection formulation of claim 21, which is stable when exposed to conditions of 40° C.±2° C./75% RH±5% RH for at least 6 months; or which is stable when exposed to conditions of 25° C.±2° C./60% RH±5% RH for at least 12 months.

26. The nimodipine injection concentrate formulation of claim 1, wherein the single hydrophilic surfactant is a polyoxyethylene sorbitan fatty acid ester.

27. The directly infusible nimodipine injection formulation of claim 21, wherein the single hydrophilic surfactant is a polyoxyethylene sorbitan fatty acid ester.

28. The nimodipine injection concentrate formulation of claim 1, wherein the single hydrophilic surfactant is polysorbate 80.

29. The directly infusible nimodipine injection formulation of claim 21, wherein the single hydrophilic surfactant is polysorbate 80.

* * * * *